(12) United States Patent
Song et al.

(10) Patent No.: US 11,045,808 B2
(45) Date of Patent: Jun. 29, 2021

(54) MICRO CHAMBER PLATE

(71) Applicant: BIONEER CORPORATION, Daejeon (KR)

(72) Inventors: Gu-Young Song, Daejeon (KR); Han Oh Park, Daejeon (KR); Won-Seok Jang, Daejeon (KR); Jung A Bae, Daejeon (KR)

(73) Assignee: BIONEER CORPORATION, Daejeon (KR)

( * ) Notice: Subject to any disclaimer, the term of this patent is extended or adjusted under 35 U.S.C. 154(b) by 221 days.

(21) Appl. No.: 15/037,672

(22) PCT Filed: Nov. 12, 2014

(86) PCT No.: PCT/KR2014/010846
§ 371 (c)(1),
(2) Date: May 18, 2016

(87) PCT Pub. No.: WO2015/076527
PCT Pub. Date: May 28, 2015

(65) Prior Publication Data
US 2016/0288120 A1 Oct. 6, 2016

(30) Foreign Application Priority Data
Nov. 20, 2013 (KR) .................. 10-2013-0141046

(51) Int. Cl.
*B01L 3/00* (2006.01)
*C12Q 1/686* (2018.01)
(Continued)

(52) U.S. Cl.
CPC .......... *B01L 3/50853* (2013.01); *C12Q 1/686* (2013.01); *B01L 2200/0689* (2013.01);
(Continued)

(58) Field of Classification Search
CPC ................ B01L 2300/0851; B01L 2200/0689
(Continued)

(56) References Cited

U.S. PATENT DOCUMENTS 4,839,280 A 6/1989 Banes et al.
5,153,136 A 10/1992 Vandenburgh
(Continued)

FOREIGN PATENT DOCUMENTS

CA 2215561 A1 3/1998
EP 1541678 A1 6/2005
(Continued)

OTHER PUBLICATIONS

Dorak, M. T., Ed., "Real-time PCR", 2006, Publisher: Taylor & Francis Group.
(Continued)

*Primary Examiner* — Natalia Levkovich
(74) *Attorney, Agent, or Firm* — Hultquist, PLLC; Steven J. Hultquist (57) ABSTRACT

The present invention relates to a micro chamber plate, and more particularly, to a micro chamber plate having micro chamber holes formed using a flowable film. Thus, samples can be injected into the micro chamber holes in a smoother manner compared to when samples are injected using a vacuum and/or centrifugal force. In addition, bubbles and excess samples in the micro chamber holes can be efficiently discharged, making it possible to perform reaction and analysis in a more accurate and efficient manner.

13 Claims, 7 Drawing Sheets

(51) Int. Cl.
*G01N 35/02* (2006.01)
*G01N 35/00* (2006.01)

(52) U.S. Cl.
CPC ..... *B01L 2200/12* (2013.01); *B01L 2200/142* (2013.01); *B01L 2300/041* (2013.01); *B01L 2300/044* (2013.01); *B01L 2300/0829* (2013.01); *B01L 2300/0848* (2013.01); *B01L 2300/12* (2013.01); *G01N 35/028* (2013.01); *G01N 2035/00277* (2013.01)

(58) Field of Classification Search
USPC .................................................. 422/552, 553
See application file for complete search history.

(56) References Cited

U.S. PATENT DOCUMENTS

| | | | |
|---|---|---|---|
| 5,948,673 | A | 9/1999 | Cottingham |
| 6,232,114 | B1 | 5/2001 | Coassin et al. |
| 6,315,957 | B1 * | 11/2001 | Feygin ............... B01L 3/50255 422/534 |
| 6,500,390 | B1 | 12/2002 | Boulton et al. |
| 2003/0103411 | A1 | 6/2003 | Fallenius |
| 2008/0210691 | A1 | 9/2008 | Yoshinari et al. |
| 2009/0010388 | A1 | 1/2009 | Stahly et al. |
| 2010/0261184 | A1 | 10/2010 | Park et al. |
| 2012/0093881 | A1 | 4/2012 | Kato et al. |
| 2012/0138221 | A1 | 6/2012 | Icke et al. |
| 2012/0276541 | A1 | 11/2012 | Lian |
| 2013/0115686 | A1 | 5/2013 | Park et al. |

FOREIGN PATENT DOCUMENTS

| | | |
|---|---|---|
| JP | 09159673 A | 6/1997 |
| JP | 10-290691 A | 4/1998 |
| JP | 2002245900 A | 8/2002 |
| KR | 10-2009-0056770 A | 6/2009 |
| WO | 0240158 A2 | 5/2002 |
| WO | 2009069886 A1 | 6/2009 |

OTHER PUBLICATIONS

Matsubara, Y., et al., "Silicon Microchamber Array for Sequence-Specific DNA Amplification and Detection Using a Novel Dispensing Method", 7th International Conference on Miniaturized Chemical and Biochemical Analysis Systems, Squaw Valley, CA, Oct. 5-9, 2003, pp. 745-748.

Leamon, J., et al., "A massively parallel PicoTiterPlate based platform for discrete picoliter-scale polymerase chain reactions", "Electrophoresis", May 29, 2003, pp. 3769-3777, vol. 24.

Nagai, H., et al., "Development of a Microchamber Array for Picoliter PCR", "Analytical Chemistry", Dec. 8, 2000, pp. 1043-1047, vol. 73, No. 5.

* cited by examiner

MICRO CHAMBER PLATE

CROSS-REFERENCE TO RELATED APPLICATIONS

This application is a U.S. national phase under the provisions of 35 U.S.C. § 371 of International Patent Application No. PCT/KR14/10846 filed Nov. 12, 2014, which in turn claims priority of Korean Patent Application No. 10-2013-0141046 filed Nov. 20, 2013. The disclosures of such international patent application and Korean priority patent application are hereby incorporated herein by reference in their respective entireties, for all purposes.

TECHNICAL FIELD

The present invention relates to a micro chamber plate, and more particularly, to a micro chamber plate having micro chamber holes formed using a flowable film, in which samples can be injected into the micro chamber holes in a more smooth manner compared to when samples are injected using a vacuum and/or centrifugal force, and in which bubbles and excess sample in the micro chamber holes can be efficiently discharged, making it possible to perform reaction and analysis in a more accurate and efficient manner.

BACKGROUND ART

As used herein, the term "micro chambers" refers to containers in which several microliters or less of minute reactions occur. These micro chambers can be formed of a silicon wafer, glass, metal, ceramic or plastic material. As used herein, the term "micro chamber plate" refers to a plate in which the micro chambers are arranged in a two-dimensional pattern and which is generally configured such that a sample can be injected into one side of the plate which can then be sealed.

Meanwhile, as a method for measuring the amount of a gene, a real-time PCR method was developed which can measure, in real time, a fluorescence value that increases in proportion to the amount of the gene, while performing a polymerase chain reaction (PCR).

The real-time PCR method can quantitatively analyze the initial concentration of a certain gene in a sample by measuring a fluorescence value generated from a PCR product for each cycle of PCR and confirming a cycle in which a certain level or more of a fluorescence value.

The real-time PCR method has advantages in that it does not require an electrophoresis process after PCR and in that it can determine the concentration of a gene having a specific nucleotide sequence in a sample in the range of $10^9$ or more by quantitatively measuring a PCR product while performing PCR ("A-Z of Quantitative PCR" edited by Stephen A. Bustin 2004-2006 International University, "Realtime PCR" edited by M. Tevfik Dorak 2006 Taylor & Francis Group).

Various types of real-time PCR devices for performing the real-time PCR method have been proposed. As a real-time PCR device capable of analyzing a plurality of samples, a device capable of analyzing 96 or 384 genes using a standard 96-well or 384-well plate was proposed (Roche, Light cycler 480, ABI 7500, 7900).

The real-time PCR device manufactured by Roche can analyze 10-50 μl of a reaction sample, and has problems in that it requires a relatively large amount of a sample and cannot analyze a large number of genes at the same time.

In an attempt to solve the above problems, various methods have been proposed which can analyze a large number of samples at the same time within a short time by reducing the amount of reaction samples using MEMS (Micro Electro Mechanical Systems) technology. Thus, methods that use a micro chamber array plate were also proposed.

The methods that use the micro chamber array plate may generally comprise the following three steps: a step of injecting reaction samples into micro chambers; a step of sealing the reaction solutions between the micro chambers; and a reaction and analysis step. First, as a method of individually adding sample solutions to the micro chambers, a micro chamber array plate was proposed. In this method, a semi-permeable membrane is covered on a transparent micro chamber plate for cell culture to isolate the micro chambers from one another, and a single cell is cultured in each of the micro chambers, followed by removal of the medium. Then, a Taqman reaction solution is added to the plate which is then sealed with transparent oil to prevent evaporation. Then, the fluorescence value at the bottom of the plate is measured while temperature cycling is performed (YASUDA, Kenji EP 1,541,678 A1, JP 2002245900 Nucleic Acid Analysis Chip and Nucleic Acid Analyzer). This method has a problem in that it is time-consuming, because different solutions are aspirated with micropipettes and added to the micro chambers. In particular, automatic micro-dispensers should be used to inject samples into 1,536 micro chambers, and a washing process that is performed before addition of different solutions is time-consuming. Thus, this method has a problem in that it is difficult to use 384 or more plates.

Second, in an attempt to solve the problems of the first method, a reactor comprising a micro chamber array manufactured using a silicon wafer by photolithography and chemical etching methods was proposed by Hidenori Nagai et al. of the professor E. Tamiya group (Anal. Chem. 200173, 1043-1047, Development of a Microchamber Array for Picoliter PCR).

The reactor uses microscope slide cover glass to prevent evaporation of a PCR solution. However, when the cover glass is attached and detached, cross-contamination of the reaction solution may occur. For this reason, a water-repellant membrane is inserted between the cover glass and the wafer, and analysis should be performed after removal of the cover glass, drying of the reaction solution and removal of the water-repellant membrane. This procedure is troublesome. In addition, there is a problem in that the reactor cannot be used for real-time quantitative amplification of a gene.

Third, in an attempt to overcome the problem of quantitative amplification, Y. Matsubara et al. of the same laboratory developed a micro chamber array manufactured by adding each primer to concave micro chambers on a wafer using a microarray system, followed by drying (7th International Conference on Miniaturized Chemical and Biochemical Analysis Systems Oct. 5-9, 2003, Squaw Valley Calif. USA).

In this micro chamber array, the upper portion of the chip is covered with mineral oil to seal the micro chamber completely, and then PCR reaction solution is added dropwise to the mineral oil using a nano-jet dispenser. According to this method, a 1,248 micro chamber array chip having a volume of 50 nanoliters (0.65×0.65×0.2 mm) is prepared using a silicon wafer (1×3 inch) by photolithography and chemical etching. Then, primers and Taqman probe solution are added dropwise to the micro chambers using a nano-liter dispenser, followed by drying. The whole chip is coated with mineral oil, and thus the micro chambers are isolated from one another and sealed.

The micro chamber array prepared using the third method has an advantage in that PCR reactions can be successfully performed in the micro chambers without cross-contamination of reaction components by dispensing a mixture of Taq DNA polymerase and sample DNA to the upper layer portion of the mineral oil in each micro chamber by use of the nanoliter dispenser.

However, the above method has disadvantages in that a separate nanoliter dispenser for a microarray is required for injection of a solution, and the dispensation process is time-consuming, and cross-contamination between reaction solutions is highly likely to occur due to flowing of the mineral oil upon movement of the plate. In addition, there are problems in that bubbles are formed at high temperatures during temperature cycling, and in that an aqueous solution becomes a spherical shape due to the hydrophobic effect of oil and the aqueous solution to cause a lens effect that causes the scattering and dispersion of excitation light and emission light during optical measurement, making measurement error bigger.

Fourth, PicoTiterPlate was developed. It is a micro chamber array manufactured by a chemical etching method like the third method, but can perform a much larger number of reactions compared to the third method (John H. Leamon et al., A massively parallel PicoTiterPlate based platform for discrete pico-liter-scale polymerase chain reactions. Electrophoresis 2003, 24, 3769-3777).

The fourth method can perform 300,000 independent PCR reactions in an amount of 39.5 µl. However, this method requires a carrier having primers/probes immobilized thereon, and thus cannot be applied to real-time quantitative PCR reactions requiring uniform optical characteristics.

Fifth, a "film reactor (or DNA card)" for reacting microsamples is disclosed in U.S. Pat. No. 5,948,673.

The film reactor comprises three very thin layers. Specifically, the lower layer film forms the bottom of the reactor, the intermediate layer film forms the side of the reactor, and the upper layer film forms a sample inlet. After a micro sample solution is injected into the film reactor using a pipette, the sample inlet should be completely sealed for reaction. If the inlet is not completely sealed, the reaction solution may be completely evaporated during PCR reaction. To treat several thousands of samples at the same time, the structure of the film reactor becomes so complicated. Thus, it is impossible to actually prepare this reactor.

Sixth, a reaction plate, which has a standard ELISA plate size and can perform 1,536 fluorescence analysis reactions, is disclosed in WO 02/40158 and U.S. Pat. No. 6,232,114.

In the sixth method, a plurality of through-holes formed in a plate, and a transparent film with weak fluorescence is attached to the plate, thereby forming a plurality of reactor vessels. Samples are placed in the vessels which are then sealed, followed by reaction. This reaction plate has transparent top and bottom sides so that excitation light can be applied to one side and fluorescence can be measured at the other side.

However, the sixth method also has problems. Specifically, to analyze a large number of genes, different primers and probes should be injected into each micro chamber. In the case of the plate for analyzing a large number of samples, several thousands of different solutions should be added to micro chambers, and for this, a special dispenser device such as a nano-liter dispenser is required. This sample injection is a time-consuming operation that frequently causes failure.

In addition, there is a problem in that, because the micro chamber cannot be completely filled with the reaction solution, bubbles are generated and water vapor is formed in the upper portion of the micro chamber upon heating to cause scattering that interferes with optical measurement.

Seventh, a reaction plate comprising a micro chamber plate is disclosed in PCT/KR2008/005635 filed in the name of the present inventors. In the micro chamber plate, a porous membrane for sample injection is formed at one side, and an optical measurement part is formed at the other side.

According to the seventh method, a plurality of through-holes is formed in the plate, and a transparent film with weak transparence is attached to one side of the plate, thereby forming a plurality of reaction vessels. Samples are placed in the reaction vessels, and then the other side of the plate is sealed with a porous membrane through which sample solutions can be injected, followed by reaction. In the reaction plate, sample solutions are injected through the porous membrane, and then mineral oil is added dropwise to the injected side to seal the side, and excitation light is applied to an optical measurement part formed at the other side, followed by measurement.

However, the seventh method has the following problems. Specifically, the structure is complex, because the injection part and the optical measurement part are formed separately. Further, the mineral oil layer formed in the injection part can become transparent, resulting in variations in measurement results according to the spot state of the bottom surface. In addition, the injection oil to which mineral oil was added dropwise for reaction and measurement can face downward, and in this case, the mineral oil having a density lower than the sample can flow into the micro chamber to cause scattering.

Recently, the present inventors developed a micro chamber plate having a new structure, which can prevent evaporation of a solution in micro chambers and facilitate sample injection to thereby significantly reduce the time required for sample injection. In addition, it can prevent a solution in the micro chamber holes from being incorporated into other adjacent chamber holes.

Additionally, it has a sample injection part integrated with an optical measurement part, so that it has a simple structure while the accuracy of measurement can be increased (see Korean Laid-Open Publication No. 2012-0010118).

However, this method has the following problems, because samples for injection are applied directly to a porous membrane. 1) When a method of injecting samples under a vacuum is used, a centrifugal force is applied in order to prevent boiling of samples upon sample application, and in this case, discharge of the samples through the pores of the porous membrane is interfered with by the surface tension of the samples and the centrifugal force. 2) Gas in the micro chambers is compressed by the centrifugal force to reduce its volume, and thus it remains as small bubbles without receiving buoyancy allowing the gas to be discharged through the membrane during injection, and is expanded again under measurement conditions at atmospheric pressure to interfere with measurement.

However, conventional micro chamber plates all have a disadvantage in that it is difficult to remove bubbles or excess sample from each micro chamber hole, and thus the accuracy of measurement is still low.

Accordingly, the present inventors have made extensive efforts to solve the above-described problems, and as a result, have found that, when micro chamber holes are formed using a flowable film, bubbles and excess sample in each micro chamber hole can be efficiently discharged after completion of sample injection so that the accuracy of measurement can be increased, thereby completing the present invention.

DISCLOSURE OF INVENTION

It is an object of the present invention to provide a micro chamber plate having micro chamber holes formed using a flowable film, in which samples can be injected into the micro chamber holes in a smoother manner compared to when samples are injected using a vacuum and/or centrifugal force, and in which bubbles and excess sample in the micro chamber holes can be efficiently discharged, making it possible to perform reaction and analysis in a more accurate and efficient manner.

In particular, the micro chamber plate according to the present invention has an advantage in that it enables complete removal of bubbles capable of remaining in each micro chamber hole when performing real-time PCR, constant-temperature enzymatic reaction or LCR (Ligase Chain Reaction), thereby significantly increasing the accuracy of optical measurement. In addition, the micro chamber plate according to the present invention has advantages in that it can prevent the evaporation of a solution in each micro chamber hole, and can shorten the time required for sample injection into each micro-hole chamber, thereby increasing the ease of solution injection, and it can perfectly prevent a solution in each micro chamber hole from being incorporated into other adjacent micro chamber holes.

Another object of the present invention is to provide a method for manufacturing the micro chamber plate and an analysis method using the micro chamber plate.

BRIEF DESCRIPTION OF THE DRAWINGS

FIG. 2 schematically illustrates a method in which a flowable film is attached closely to a micro chamber body, followed by injection of a sample wherein: (A) shows a state in which a flowable film is attached closely to a micro chamber body; (B) shows a state in which micro chamber holes are formed by applying heat, vacuum or pressure to the micro chamber body having the flowable film attached thereto to thereby form cylindrical optical measurement parts; (C) shows a state in which micro chamber holes are formed by applying heat, vacuum or pressure to the micro chamber body having the flowable film attached thereto to thereby form hemispherical optical measurement parts; (D) shows a state in which a specific component is injected in the micro chamber holes; (E) shows a state in which a micro chamber body covering part is attached to the top side of the micro chamber body; (F) shows a state in which a sample is injected in the micro chamber holes by a vacuum and/or centrifugal force (the micro chamber holes include bubbles); and (G) shows a state in which bubbles in the micro chamber holes were discharged and removed by shrinkage of the flowable film after removal of the vacuum and/or centrifugal force.

FIG. 3 schematically illustrates a method in which a flowable film and an adhesive film are attached closely to a micro chamber plate, followed by injection of a sample; wherein: (A) shows a state in which a flowable film and an adhesive film are attached closely to the micro chamber body; (B) shows a state in which micro chamber holes are formed by applying heat, vacuum or pressure to the micro chamber body having the flowable film and adhesive film attached thereto to thereby form cylindrical optical measurement parts; (C) shows a state in which micro chamber holes are formed by applying heat, vacuum or pressure to the micro chamber body having the flowable film and adhesive film attached thereto to thereby form hemispherical optical measurement parts; (D) shows a state in which a specific component is injected in the micro chamber holes; (E) shows a state in which a micro chamber body covering part is attached to the top side of the micro chamber body; (F) shows a state in which a sample is injected in the micro chamber holes by a vacuum and/or centrifugal of the flowable film after removal of the vacuum and/or centrifugal force; and (G) shows a state in which bubbles in the micro chamber holes were discharged and removed by shrinkage of the flowable film after removal of the vacuum and/or centrifugal force.

BEST MODE FOR CARRYING OUT THE INVENTION

Unless otherwise defined, all technical and scientific terms used herein have the same meaning as commonly understood by one of ordinary skill in the art to which the invention pertains. Generally, the nomenclature used herein are well known and commonly used in the art.

Figure 1:
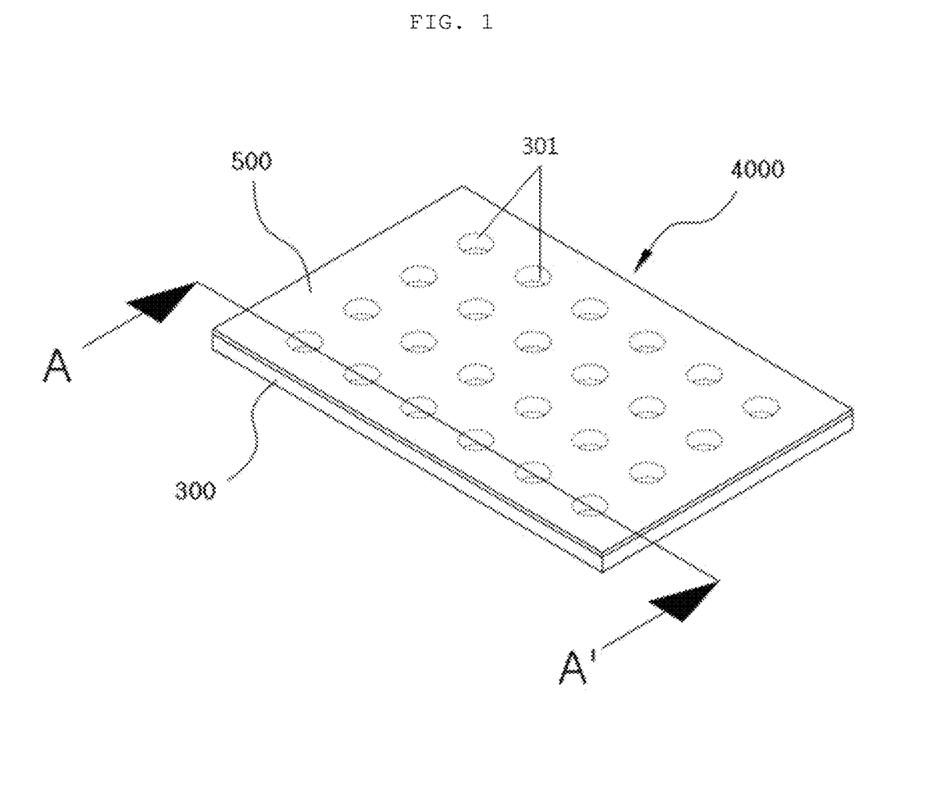
FIG. 1 is a perspective view of a micro chamber plate manufactured by attaching a flowable film and a micro chamber body covering part.
Figure 2:
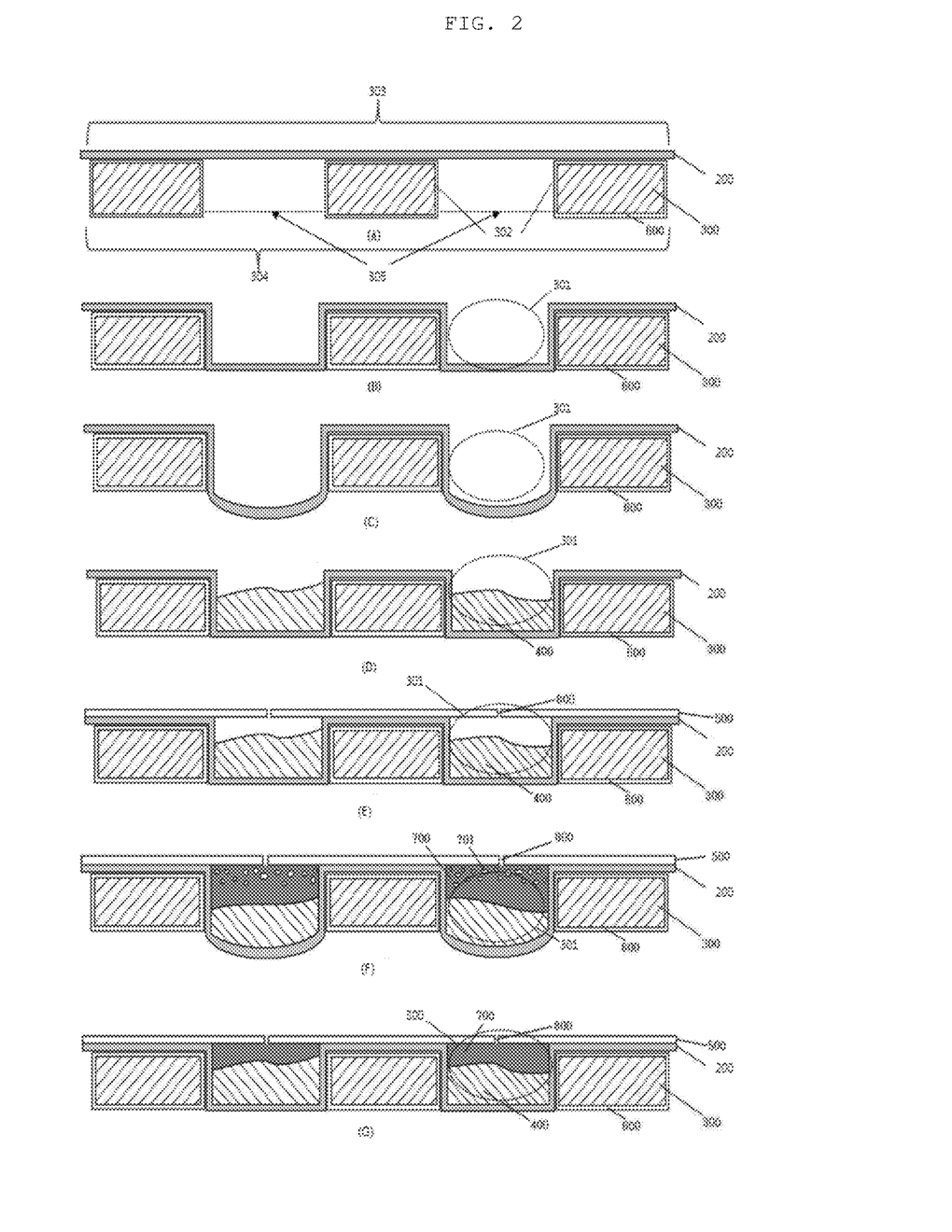
Figure 3:
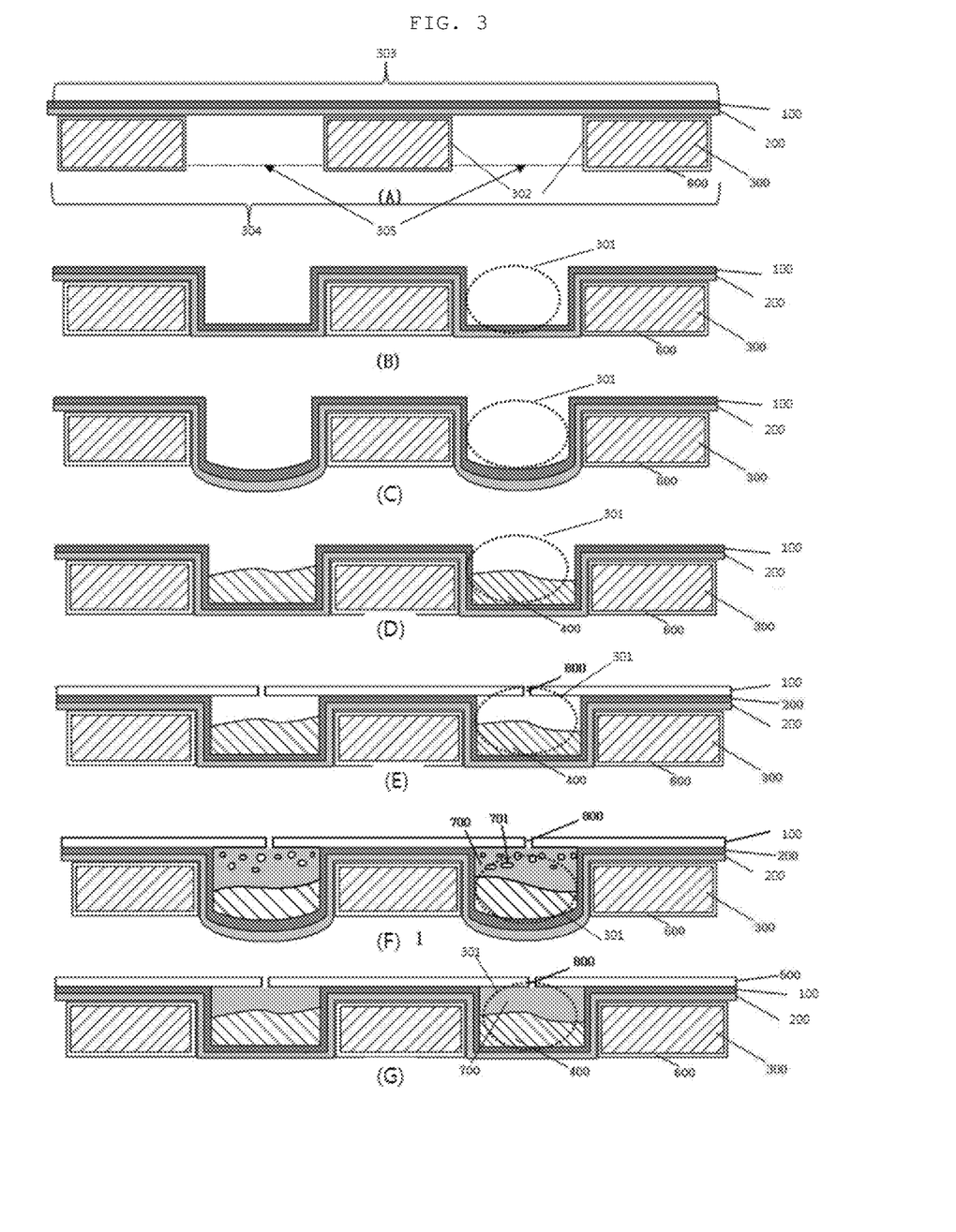

Referring to the figures, and particularly to FIGS. 1-3, the present invention provides a micro chamber plate as illustratively shown in FIG. 1 as micro chamber plate 4000, comprising: a micro chamber body 300; and a micro chamber body covering part 500 provided on the top side 303 of the micro chamber body 300, the micro chamber plate having formed therein a predetermined number of micro chamber holes 301 suitable to retain a specific component for analysis of a biological substance, wherein a portion or all of the bottom side 304 of the micro chamber body, particularly the bottom side 305 of each of the micro chamber holes 301, is made of a flowable film 200.

The flowable film 200 is attached closely to the micro chamber body 300 to form transparent optical parts. When a sample is injected by application of a vacuum and/or centrifugal force, the flowable film 200 is stretched in the direction of action of the centrifugal force (occurrence of sagging), and air in the micro chamber holes 301 is discharged by application of a vacuum so that samples can be introduced in a smooth manner. When the vacuum and centrifugal force are removed, the flowable film 200 is restored to its original shape (removal of sagging), and at the same time, excess sample or bubbles in each micro chamber hole 301 can be smoothly discharged through sample inlets 800.

As used herein, the term "flowable film 200" means a film having the property of freely changing its shape due to its flexibility when heat, a vacuum or pressure is applied thereto. Particularly, the flowable film 200 preferably has the property of being stretched (i.e., sagged) in the direction in which an applied centrifugal force of 10-1000 G, preferably 300-700 G, more preferably 400-600 G, acts.

The flowable film 200 may be formed only on the bottom side 304 of the micro chamber body, and may also be formed on both the bottom side 304 and the top side 303 of the micro chamber body. Particularly, the flowable film 200 is preferably formed to extend from the top side 303 of the micro chamber body through the lateral side 302 of the micro chamber holes to a portion or all of the bottom side 304 of the micro chamber body, particularly the bottom side 305 of the micro chamber holes 301. The flowable film 200 is attached closely to the micro chamber body to form transparent optical parts and the micro chamber holes.

Specifically, if the flowable film 200 is to be formed only on the bottom side 304 of the micro chamber body, the flowable film may be formed all over the bottom side of the micro chamber body, including the bottom side 305 of the micro chamber holes 301. If the flowable film 200 is to be formed to extend from the top side 303 of the micro chamber body through the lateral side 302 of the micro chamber holes to the bottom side 305 of the micro chamber holes 301, the flowable film is preferably formed only on the bottom side 305 of the micro chamber holes 301 in the bottom side 304 of the micro chamber body.

To form the flowable film 200 to the bottom side 304 of the micro chamber body, the flowable film 200 may also be attached directly to the bottom side 304 of the micro chamber body, but the flowable film 200 is preferably attached closely to the top side 303 of the micro chamber body, and then blow-molded at a temperature of 100 to 300° C., preferably 110 to 270° C., so that it is formed to extend through the lateral side 302 of the micro chamber holes to a portion or all of the bottom side 304 of the micro chamber body, particularly the bottom side 305 of the micro chamber holes 301. In addition, pressure and/or a vacuum is preferably additionally applied during the blow molding process. By doing so, micro chamber holes 301 are formed which are internal spaces made of the flowable film 200, which can be injected with specific components for analysis of biological substances, samples, and the like.

In the present invention, as the material of the flowable film 200, any material may be used without limitation, as long as it is transparent such that it allows optical measurement. Preferably, the flowable film 200 may be made of one polymer or a copolymer of two or more selected from the group consisting of polyethylene, polyethylene terephthalate, stretched or non-stretched polypropylene, polycarbonate, PMMA. In addition, the thickness of the flowable film 200 is preferably 200 μm or less, particularly 100 μm or less, but is not limited thereto.

In the present invention, in order to facilitate the attachment of the micro chamber body covering part 500 to the flowable film 200, an adhesive material may be applied to the surface of the micro chamber body covering part, or an adhesive film 100 having an adhesive property may additionally be provided between the flowable film 200 and the micro chamber body covering part 500. In addition, in order to facilitate the attachment of the flowable film 200 to the micro chamber body 300, an adhesive material may be applied to the surface of the micro chamber body to form an adhesive coating layer 600, or an adhesive film 100 having an adhesive property may additionally be provided between the flowable film 200 and the micro chamber body 300.

The adhesive film 100 and the adhesive material are preferably transparent such that they can form an optical measurement part together with the flowable film, but these materials may also be materials that are permeable or selectively permeable to light having a certain wavelength. The adhesive material that is used in the present invention may preferably be a polyethylene-based film type hot-melt adhesive, and the adhesive film may be, for example, a product such as ZPMA-film001 (Pinghu Zhanpeng Hot Melt Adhesive Web & Film Co., Ltd.), but is not limited thereto.

As used herein, the expression "specific components for analysis of biological substances" means primers, probes, antibodies, aptamers, DNA or RNA polymerases, etc., which are used for the quantitative or qualitative analysis of specific biological substances, for example, proteins, DNAs, RNAs, etc. Particularly, the expression means components required to perform real-time PCR, constant-temperature enzymatic reaction or LCR (ligase chain reaction). Particularly, the expression "specific components for analysis of nucleic acids" means primers, probes, antibodies, aptamers, DNA or RNA polymerases, etc., which are used for the quantitative or qualitative analysis of DNAs or RNAs.

As the samples that are used in the present invention, analytes for quantitative or qualitative analysis may be used alone depending on the type of micro chamber plate manufactured, or analytes may be used after addition to components for real-time PCR reaction. The components for performing real-time PCR include, but are not limited to, reaction buffer, $MgCl_2$, four kinds of dNTPs, DNA or RNA polymerase, etc., and conventional components required for real-time PCR may also be used. For hot-start real-time PCR, pyrophosphate, pyrophosphatase or the like may additionally be used.

In the present invention, the micro chamber body covering part 500 may be made of a metal, a polymer film, a plastic material, a porous membrane or the like, but is not limited thereto. Specifically, the micro chamber body covering part 500 may be made of any material which has a hardness such that it can be attached to the micro chamber body 300 or the flowable film 200 such that a specific component 400 for analysis of biological substances or a sample 700 can be maintained in the micro chamber holes 301, and which has no reactivity with the specific component 400 for analysis of biological substances or the sample 700, which are contained in the micro chamber holes 301. Particularly, the micro chamber body covering part 500 may be made of a porous membrane having a pore size of 0.2-5.0 μm. Preferably, the micro chamber body covering part 500 may be in the form of a film such as an aluminum, stainless steel, polyethylene, polypropylene, polycarbonate, PMMA, polystyrene, nylon or polyurethane film, or may be made of a porous membrane such as a polyethylene, polypropylene, polycarbonate, PMMA, nylon, PTFE or PVDF membrane.

The micro chamber body covering part 500 may have a thickness of 5-400 μm, preferably 10-200 μm. To increase the optical measurement efficiency, the micro chamber body covering part 500 is preferably made of a light reflective material or surface-coated or modified so as to be able to reflect light.

In addition, the micro chamber body covering part 500 is attached to the micro chamber body 300 by the flowable film 200, and serves to prevent samples or specific components for analysis of biological substances, injected in the micro chamber holes 301, from flowing to the outside.

Preferably, the micro chamber body covering part 500 has formed therein at least one sample inlet 800 per micro chamber hole 301. Each sample inlet 800 may be formed differently depending on the area of the micro chamber hole 301. Specifically, it preferably has an area of 0.05-60% based on the total area of each micro chamber hole (the area of the top portion coming in contact with the micro chamber body covering part 500), but is not limited thereto. In the present invention, if the micro chamber body covering part 500 is made of a metal, the sample inlet 800 may be formed by etching, and if the micro chamber body covering part 500 is made of a polymer film, the sample inlet 800 may be formed by punching, but is not limited thereto.

As described above, in the present invention, the micro chamber body covering part 500 may be attached to the top layer portion of the flowable film 200, and an adhesive film 100 having an adhesive property may additionally be introduced between the micro chamber film sealing part 500 and the flowable film 200. Herein, the adhesive film may be introduced by a method such as thermal bonding, ultrasonic bonding, or adhesive agent application. If the micro chamber body covering part 500 is to be attached by heating, it is preferably heated to a temperature of 100 to 170° C., preferably 110 to 160° C., more preferably 120 to 150° C., so that it can be easily attached closely. After close attachment, a sample 700 is injected by application of a vacuum and/or centrifugal force. Then, the sample inlet 800 may be sealed using at least one material selected from the group consisting of a polymer film, oil, silicone, paraffin and an adhesive agent.

In the present invention, the micro chamber body 300 is preferably made of a metal or polymer material, more preferably SUS (stainless steel). Particularly, the surface of the micro chamber body 300 is preferably coated with at least one material selected from among a polyester-based polymer resin and a polyethylene-based hot-melt adhesive to form an adhesive coating layer 600, so that the adhesion of the flowable film 200 is increased to prevent separation of the flowable film 200 and the side of the flowable film 200 is attached to the micro chamber body 300 so that the sagging of the flowable film 200 by a centrifugal force is limited only to the direction of the centrifugal force. Coating of the surface of the micro chamber body may be performed by a conventional method known in the art, such as spray coating, dip coating or roller coating.

In another aspect, the present invention provides a method for manufacturing the micro chamber plate.

The method for manufacturing the micro chamber plate according to the present invention comprises the steps of:

(a) attaching a flowable film 200 closely to the top side 303 of the micro chamber body;

(b) performing blow molding to attach the flowable film 200 closely to the side 302 of each micro chamber hole and, at the same time, form the flowable film 200 at the bottom side 305 of the micro chamber hole, thereby forming the micro chamber holes 301; and (c) attaching a micro chamber body covering part 500 to the flowable film 200 on the top side 303 of the micro chamber body.

In the method for manufacturing the micro chamber plate, the micro chamber body 300, the flowable film 200, the micro chamber body covering part 500 and the like have the technical characteristics as described above.

The method for manufacturing the micro chamber plate may further comprise, between steps (b) and (c), step (b') of injecting a specific component 400 for analysis of biological substances into each micro chamber hole 301. The blow molding in step (b) may be performed at a temperature of 100° C. to 300° C., preferably 110° C. to 270° C. Furthermore, step (b) of performing the blow molding may further comprise a step of applying a vacuum and/or pressure to form the micro chamber holes. In addition, the method for manufacturing the micro chamber plate may further comprise, after step (c), the steps of: (d) injecting the sample 700; and (e) sealing the sample inlets 800.

EXAMPLES

Hereinafter, examples of the present invention will be described in further detail with reference to the accompanying drawings. A description of technical content that is well known to those skilled in the art and is not directly related to the present invention is omitted when examples of the present invention are described. The reason for this is to omit unnecessary description, and to more definitely transmit the gist of the present invention rather than making the gist of the present invention unclear.

Example 1

Manufacture of Micro Chamber Plate 1-1: Preparation of Micro Chamber Body 300

Stainless steel (SUS) having a predetermined thickness was etched to prepare a micro chamber body 300 having certain spaces (i.e., micro chamber holes 301) formed therein. The stainless steel (SUS) forming the micro chamber body 300 had a thickness of 1 mm, and the chamber holes 301 had a diameter of 1.2-1.9 mm. The chamber holes 301 were formed at intervals of 2.25 mm, and up to 768 chamber plates 301 were formed per plate. The diameter of the chamber holes 301 and the interval between the chamber holes 301 can be easily controlled.

1-2: Attachment of Flowable Film 200 to Micro Chamber Plate 300

The flowable film 200 may be made of one or a combination of two or more selected from among polyethylene, polyethylene terephthalate, polypropylene, polymethyl methacrylate, and polycarbonate. Any transparent moldable film may be used for the flowable film 200. Hereinafter, the use of a cast polypropylene film (GCP, 60 μm, YoulChon Chemical, Co., Ltd., Korea) as the cast flowable film 200 will be described by way of example.

To attach the flowable film 200 closely to the top side 303 of the micro chamber body, a liquid hot-melt (427T, Aerochem Co., Ltd.) diluted in MEK at a concentration of 3-5 vol % was spray-coated on the micro chamber body 300. The liquid hot-melt serves to fix the flowable film 200 to the micro chamber body 300 so that the flowable film 200 is not separated from the micro chamber body. Next, the cast polypropylene film (GCP, 60 μm, YoulChon Chemical, Co., Ltd., Korea) and an adhesive film (ZPMA-film001, Pinghu Zhanpeng Hot Melt Adhesive Web & Film Co., Ltd.) were cut to a size corresponding to a micro chamber plate, and the micro chamber body, the CPP film and the adhesive film were sequentially deposited on a blow molding device.

The flowable film 200 in the present invention is formed to be attached to the top side 303 of the micro chamber body and the side 302 of each micro chamber hole. It is formed to extend from the top side 303 of the micro chamber body to the bottom side 304 of the micro chamber body, particularly the bottom side 305 of the micro chamber holes 301, so as to define each micro chamber hole 301. It serves to protect the inside of each micro chamber hole and to separate the micro chamber holes from one another and also to allow the micro chamber body covering part 500 to be attached to the top side 303 of the micro chamber body.

The flowable film 200 made of a transparent film is located on the side opposite the inlet portion to form an optical measurement part. The flowable film 200 may preferably be made of a film selected from among polyethylene, polyethylene terephthalate, stretched or non-stretched polypropylene, polycarbonate, PMMA, and copolymers thereof. This film may be attached closely to the micro chamber body 300 by application of a vacuum and pressure and, at the same time, may form a transparent optical measurement part, thereby forming micro chamber holes 301.

1-3: Formation of Micro Chamber Holes Using Flowable Film

After the flowable film 200 was attached to the micro chamber body as described in Example 1-2, blow molding was performed at a temperature of 170 to 270° C. under a vacuum (−20 kPa to −100 kPa) or pressure (1-2 kgf/cm$^2$), thereby forming the flowable film 200 on the side 302 of the micro chamber holes and the bottom side 304 of the micro chamber body. When the vacuum or pressure was applied, the molding device was closed so that leakage would not occur. At 1 hour after completion of the blow molding, the molding device was cooled with cold water, and the micro chamber body having the flowable film formed thereon was separated from the molding device. An excess of the flowable film formed on the micro chamber body was cut according to the shape of the micro chamber body.

1-4: Dispensation of Specific Component 400 into Micro Chamber Holes 301

A specific component 400 for nucleic acid analysis was dispensed into each micro chamber hole 301 formed in the micro chamber body. The specific component 400 includes each primer or probe. Dispensation of the specific component was performed using a sample dispenser, and 1-2 μl of a sample was dispensed into each micro chamber hole 301 at the concentration calculated for reaction. The dispensed specific component 400 was dried in an oven at 80-90° C. for 5 minutes to prevent its separation from the micro chamber holes 301.

1-5: Attachment of Micro Chamber Body Covering Part 500 to Micro Chamber Body 300

To the micro chamber body 300 having the micro chamber holes 301 including different specific components, a micro chamber body covering part 500 having sample inlets 800 formed therein was attached. The micro chamber body covering part 500 has a thickness of 10-200 μm and may be in the form of a film such as an aluminum, stainless steel, polyethylene, polypropylene, polycarbonate, PMMA, polystyrene, nylon or polyurethane film, or may be made of a porous membrane such as a polyethylene, polypropylene, polycarbonate, PMMA, nylon, PTFE or PVDF membrane, or may be formed of a metal.

Figure 6:
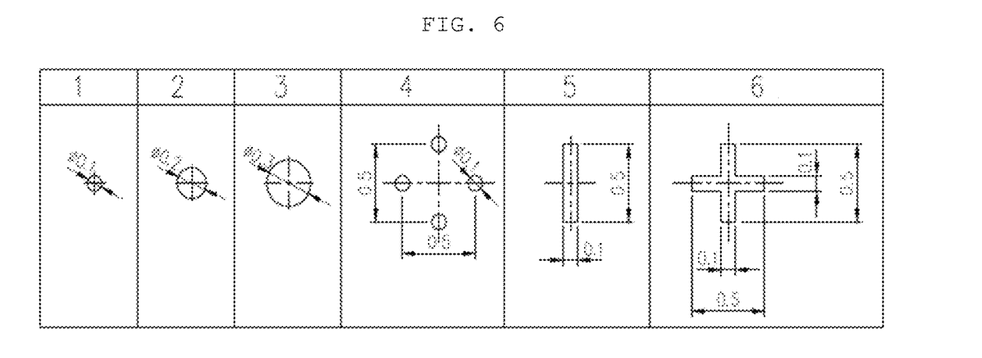
FIG. 6 illustrates the shape of a sample inlet which is formed in a micro chamber body covering part.
Figure 7:
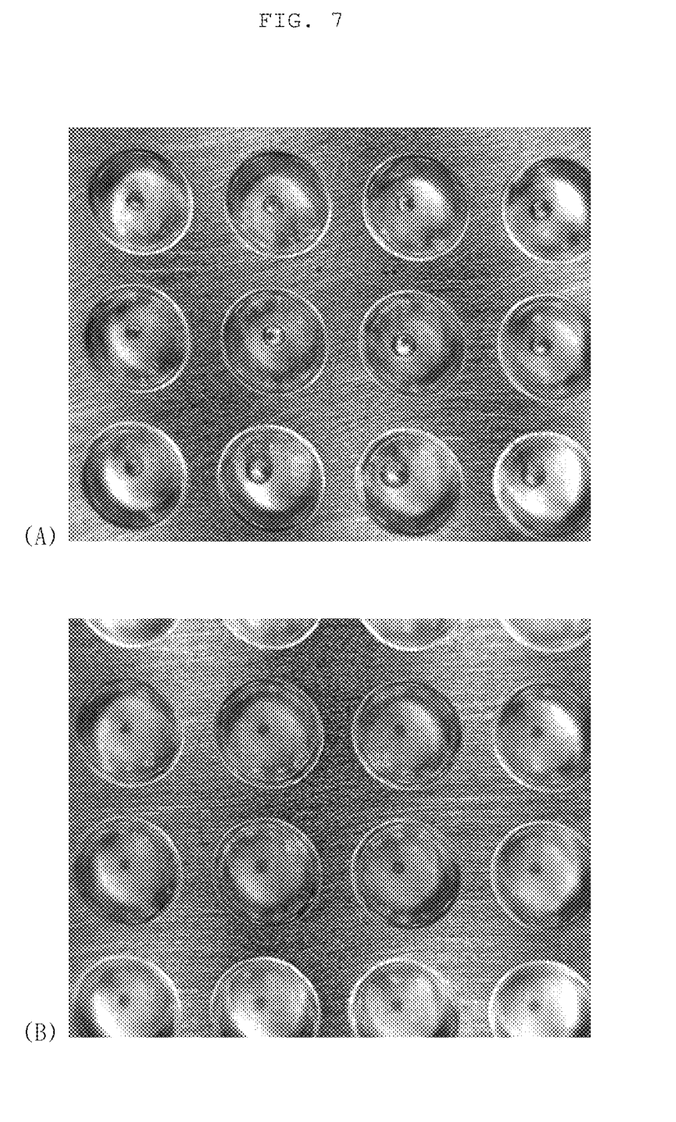
FIG. 7 shows a state in which bubbles were discharged after sample injection into micro chamber holes, wherein the photographs in FIG. 7 are photographs at about 60× magnification, and the black points in the center indicate the appearance of sample inlets, and wherein: (A) is a photograph showing a state in which bubbles were formed in micro chamber holes when samples were injected into a conventional micro chamber plate; and (B) is a photograph showing a state in which samples were injected into micro chamber holes without bubbles when the samples were injected into a micro chamber plate according to the present invention.

If the micro chamber body covering part 500 is formed of a metal or a film, the sample inlet 800 has one or more injection holes for sample injection. The injection hole consists of a point or line having an area corresponding to 0.05-60% of the area of each micro chamber hole, and may preferably have the shape shown in FIG. 6.

In the case of the film-type micro chamber body covering part 500, a pattern that isolates between the micro chambers may be formed so that a sample solution in one micro chamber is prevented from being incorporated into other adjacent micro chambers, even when a portion of the sample 700 flows out during injection of the sample 700 and sealing of the injection hole.

In addition, if the micro chamber body covering part 500 is made of a porous membrane, it may be a transparent or semi-transparent polymeric porous membrane having a pore size of 0.2-5.0 μm. In the present invention, a 50 μm thick stainless steel having a 200 μm sample inlet 800 formed by etching was used. The micro chamber body covering part 500 is attached to the surface of the flowable film 200 formed on the micro chamber body so as to cover the top side of the micro chamber body, thereby forming an independent micro chamber.

Attachment of the micro chamber body covering part 500 may be performed depending on the material and structure of the flowable film 200 attached to the micro chamber body 300. If the flowable film 200 is made of one kind of film, an adhesive agent may be applied to the flowable film 200 and cured. If the flowable film is made of a combination of two or more films, attachment of the micro chamber body covering part 500 may be achieved by ultrasonic bonding or thermal compression.

The adhesive agent may be a room-temperature curable adhesive, a thermosetting adhesive, a reaction curable adhesive, etc., and is preferably one that is insoluble in water and has thermal stability.

In the case of ultrasonic bonding or thermal bonding, it is preferably performed at a temperature at which a portion of the flowable film 200 can be melted while the flowable film 200 attached to the micro chamber body 300 is not deformed. In the present invention, the micro chamber body covering part 500 was attached by thermal compression at 150° C. for 5 seconds or less or by roll compression. In addition, ultrasonic bonding may be performed at any temperature, because heat generated on the attachment side is not transferred into the micro chambers.

Preferably, after attachment of the micro chamber body covering part 500, cooling and post-compression processes may further be performed to secure the attachment of the micro chamber body covering part 500.

Example 2

Injection of Sample Through Sample Inlet

A process of vacuum-injecting a sample into each micro chamber hole 301 through the sample inlet 800 formed in the micro chamber body covering part 500 will now be described in detail. Herein, the sample may be different between the micro chamber holes 301, and the same sample may be injected into some or all of the micro chamber holes.

When the sample 700 is injected into the micro chamber holes 301, air in the micro chamber holes 301 can be smoothly removed by removing air from the micro chamber holes 301 by use of a vacuum and a centrifugal force and then brining the sample 700 into contact with the micro chamber holes. By doing so, the sample 700 is completely injected without air bubbles.

However, if a vacuum state is maintained for a long time even when air is removed from the micro chamber holes 300, evaporation of the sample 700 can occur, and if a sufficient level of vacuum is not applied, there is a limit to the complete removal of the remaining bubbles.

For this reason, in the present invention, the flowable film 200 that can be stretchable by a centrifugal force is formed so that a sufficient amount of the sample 700 can be injected, thereby making it possible to perfectly inject the sample 700.

The flowable film 200 can be sagged by the centrifugal force, and for this reason, the internal volume can increase so that a sufficient amount of the sample 700 can be supplied through the sample inlet. When the centrifugal force is removed, the sagging is relived so that an excess of the sample can be discharged to the outside of the micro chamber holes 301 while bubbles 701 capable of remaining in the micro chamber holes 301 can be completely discharged to the outside of the micro chamber holes 301 through the sample inlet 800, thereby making it possible to perfectly inject the sample.

In the present invention, a vacuum was applied for less than 1 minute and 30 seconds at a centrifugal force of 50 G or less, after which the sample 700 was injected at 450 G or more while the vacuum state was maintained. The centrifugal force is preferably a centrifugal force sufficient to cause the sagging of the flowable film. In the present invention, a centrifugal force of 450 G or more was used to cause sufficient sagging of the flowable film.

After the completion of sample injection, the sample inlet 800 formed in the micro chamber body covering part 500 was sealed in order to prevent the sample from flowing out through the sample inlet 800. Preferably, the sample inlet 800 may be sealed with a polymeric film, oil, silicone, paraffin, an adhesive, or the like. In the present invention, the sample inlet 800 was sealed by attaching a polymeric film thereto.

In the present invention, a HBV kit (Bioneer, AccuPower® HBV Quantitative PCR Kit) was used as a sample. Specifically, 0.5 μl of an internal positive control (IPC), 0.5 μl of a positive control (PC) and distilled water (D.W.) were added to a dry sample for a 96-well plate, and the total volume of the mixture was adjusted to 50 μl. Then, the mixture was injected into each micro chamber hole of the micro chamber plate of the present invention by use of a dispenser, thereby completing the micro chamber plate.

The micro chamber plate manufactured in the Example of the present invention was used to confirm whether PCR would be properly performed in the micro chamber plate. The step of injecting specific components as described in Example 1-4 was omitted, and IPC and PC together with the sample were injected into the micro chamber plate. Herein, the PC used serves as an analyte in this experiment to confirm the results of amplification.

Example 3

Carrying Out of Polymerase Chain Reaction (PCR) and Quantitative Analysis

Using the micro chamber plate manufactured in Example 2, a polymerase chain reaction (PCR) was performed. From the results of the PCR reaction, it was found that gene amplification could be performed in the micro chamber plate of the present invention.

Figure 8:
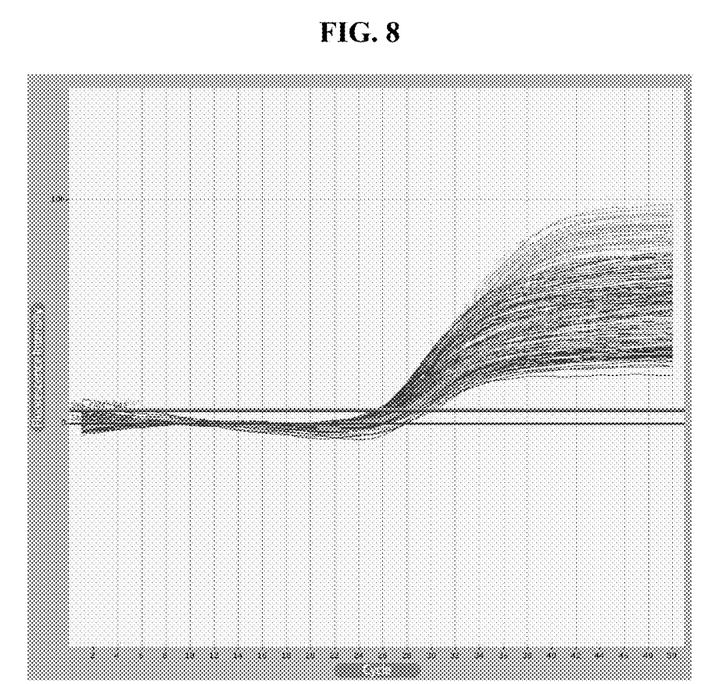
FIG. 8 is a graph showing the results of a polymerase chain reaction performed using a micro chamber plate of the present invention. The results in FIG. 8 indicate that gene amplification occurred.
Figure 9:
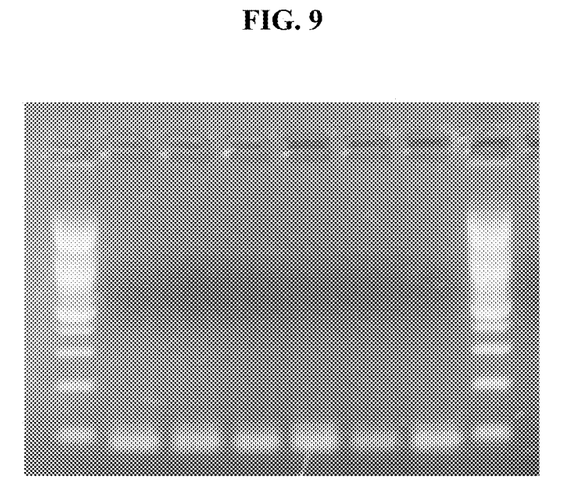
FIG. 9 shows the results of SDS-PAGE gel electrophoresis of the product of a polymerase chain reaction performed using a micro chamber plate of the present invention.

Using an amplification system described in Korean Patent No. 10-1089045, a real-time polymerase chain reaction (PCR) was performed. Conditions for the PCR are shown in Table 1 below. The temperature and time in the PCR reaction are not limited to those described in this Example, and can be changed to other conditions suitable for PCR reactions. The PCR reaction was performed under the following conditions: stabilization at 25° C. for 1 min, and then denaturation at 95° C. for 5 min, followed by 50 cycles, each consisting of 95° C. for 5 sec and 55° C. for 10 sec. The results of the PCR reaction are shown in FIGS. 8 and 9. As can be seen in FIG. 8, as the cycles of the PCR reaction proceeded, the measured fluorescence value increased, and a typical amplification curve appeared, indicating that amplification occurred in all the chambers of the micro chamber plate. In addition, SDS-PAGE electrophoresis was performed in order to confirm the amplification product, and the results of the SDS-PAGE electrophoresis are shown in FIG. 9. As shown in FIG. 9, a band could be seen at the position of amplification of the PC (positive control), indicating that normal amplification occurred (Marker: Bioneer, 25/100 bp Mixed DNA Ladder). From such results, it was found that normal gene amplification is possible in the micro chamber plate of the present invention.

TABLE 1

| Polymerase chain reaction conditions Protocol information | | | | |
|---|---|---|---|---|
| Step | Function | Temperature | Time (hh:mm:ss) | Repeat |
| 1 | INCUBATE | 25.00 | 00:01:00 | 0 |
| 2 | INCUBATE | 95.00 | 00:05:00 | 0 |
| 3 | INCUBATE | 95.00 | 00:00:05 | 0 |
| 4 | INCUBATE | 55.00 | 00:00:10 | 0 |
| 5 | SCAN | | | 0 |
| 6 | GOTO | Step3 | | 50 |
| 7 | INCUBATE | 20.00 | 00:03:00 | 0 |

Example 4

Use of Micro Chamber Plate

Figure 4:
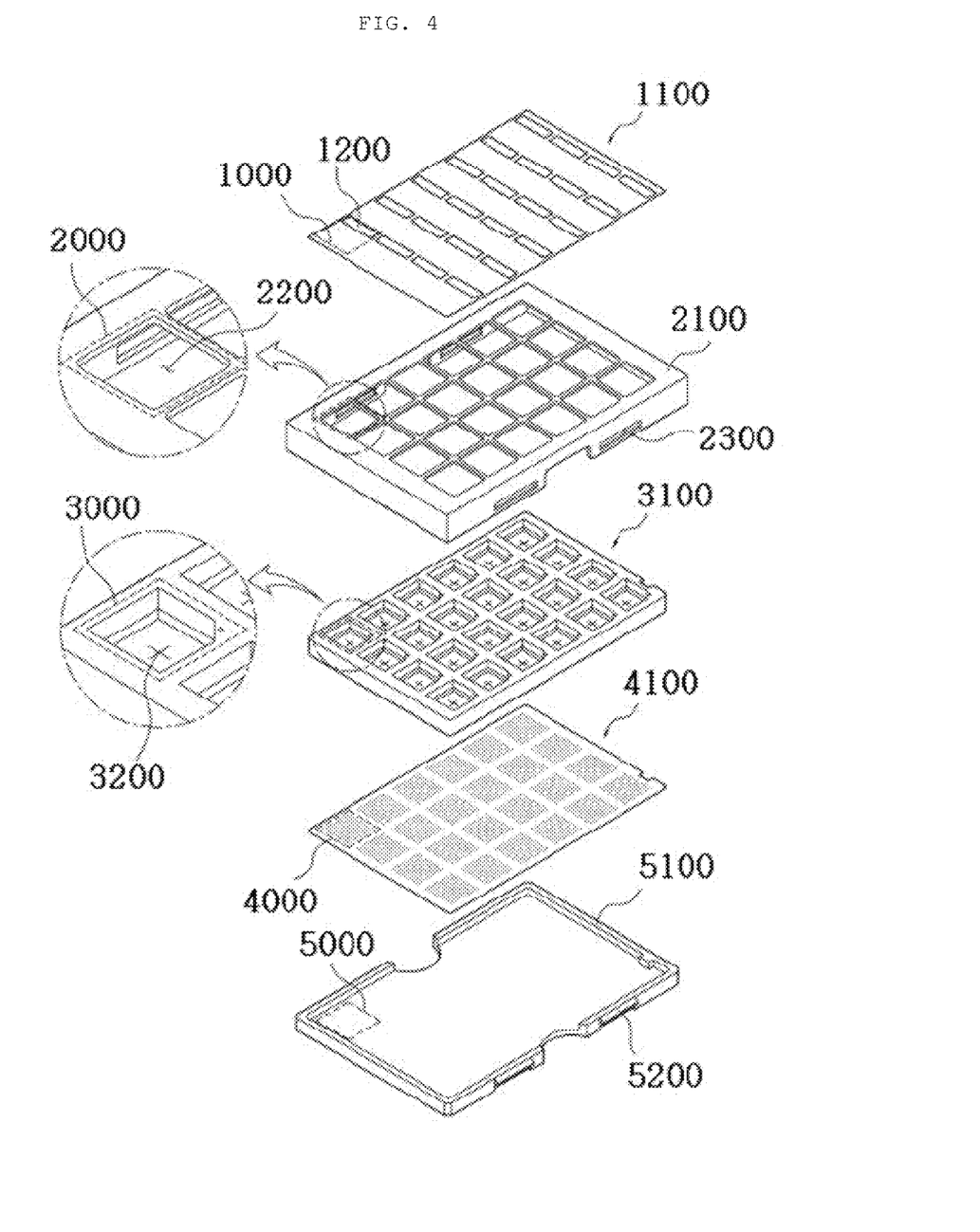
FIG. 4 is an exploded perspective view of a polymerase chain reaction (PCR) chamber including a manufactured micro chamber plate.
Figure 5:
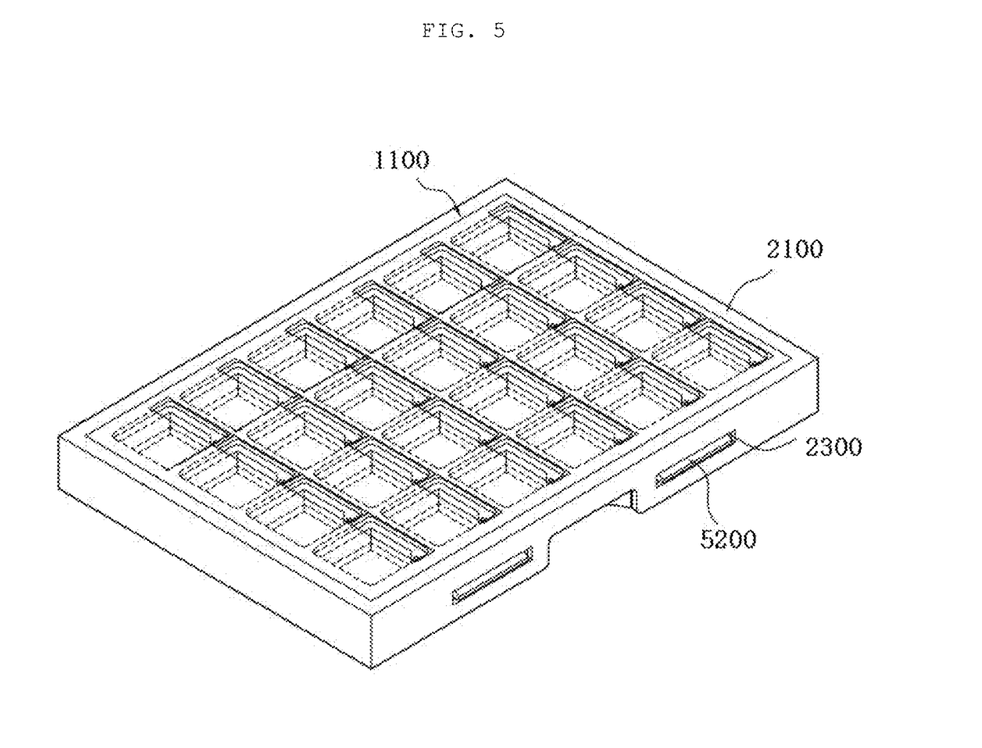
FIG. 5 shows the shape of a polymerase chain reaction (PCR) chamber including a manufactured micro chamber plate.

Hereinafter, the use of the micro chamber plate according to the present invention will be described with reference to FIGS. 4 and 5. The micro chamber plate according to the present invention may be received in a micro chamber plate receiving part 5000. The micro chamber plate receiving part 5000 may be in the form of a flat plate. The micro chamber plate receiving part 5000 is configured to mount thereon a micro chamber plate 4000 for sample injection. Reference numeral 5100 indicates a micro chamber plate receiving part module having formed therein a plurality of micro chamber plate receiving parts 5000. Meanwhile, on the side of the micro chamber plate receiving part module 5100, a receiving g part locking protrusion 5200 is formed. Reference numeral 3100 in FIG. 4 indicates a micro chamber plate receiving part cover module having formed therein a plurality of micro chamber plate receiving part covers 3000 connected to one another.

In addition, at the bottom side of the micro chamber plate receiving part cover 3000, a chamber communicating portion is formed. The chamber communicating portion may be an incision line 3200 that is widened by an external force. When a centrifugal force is applied to the incision line, the incision line is widened by pressure so that the sample solution to be injected can be introduced into the micro chamber hole through the incision line. If an external force does not act on the bottom side of the micro chamber plate receiving part cover 3000, the nucleic acid-containing sample solution temporarily stored in the micro chamber plate receiving part cover 3000 will not flow out of the micro chamber plate receiving part cover 3000 through the incision line 3200. The micro chamber plate receiving part cover 3000 may be made of a silicone material. Meanwhile, the incision line 3200 may have a "+" shape, a "<" shape, a "=" shape, or a "x" shape.

The micro chamber plate receiving part may be locked to a locking case 2000. In the locking case 2000, a through-hole 2200 is formed. Reference module 2100 indicates a locking case module having formed therein a plurality of locking cases connected to one another. Meanwhile, on the side of the locking case set 2100, a case locking groove 2300 into which the receiving part locking protrusion 5200 is inserted is formed. The locking case 2000 is pressed against the top of the micro chamber plate receiving part cover 3000 and is locked to the micro chamber plate receiving part. Locking between the locking case 2000 and the micro chamber plate receiving part 5000 is achieved by inserting the receiving part locking protrusion 5200 into the case locking groove 2300. As the locking case 2000 is locked to the micro chamber plate receiving part 5000, the bottom end of the cover support portion is attached closely to the top end of the micro chamber plate 4000 for sample injection, and thus a sample solution storage space is formed between the micro chamber plate receiving part cover 3000 and the micro chamber plate 4000 for sample injection. As the locking case 2000 is locked in the micro chamber plate receiving part 5100, the lower end of the through-hole communicates with the sample solution storage space, and the case through-hole 2200 communicates with the micro chamber plate receiving part cover 3000.

The case cover 1000 is attached to the locking case 2000. In the case cover 1000, a case cover through-hole 1200 is formed. The case cover through-hole 1200 is formed such that the case cover 1000 covers a portion of the micro chamber plate receiving part cover 3000 when it is attached to the locking case 2000. Reference numeral 1100 indicates a case cover module having formed therein a plurality of case covers 1000 connected to one another.

INDUSTRIAL APPLICABILITY

As described above, the micro chamber plate comprising the flowable film according to the present invention has an advantage in that it enables complete removal of bubbles and excess sample from each micro chamber hole when performing real-time polymerase chain reaction (PCR), constant temperature enzymatic reaction or LCR (ligase chain reaction), thereby significantly increasing the accuracy of optical measurement. See FIG. 2 hereof. In addition, it can prevent evaporation of a solution in each micro chamber hole, and can shorten the time required for sample injection into each micro chamber hole, thereby increasing the ease of solution injection, and it can perfectly prevent a solution in each micro chamber from being incorporated into other adjacent micro chambers.

In addition, the present invention has advantages in that a small amount of a sample can be analyzed in various ways depending on a specific component injected into the micro chamber hole 301 and in that a plurality of samples can be analyzed using a single micro chamber plate.

What is claimed is:

1. A micro chamber plate comprising:
    a micro chamber plate body;
    a micro chamber plate body covering part provided on a top side of the micro chamber plate body; and
    micro chamber holes in the micro chamber plate body capable of having therein a specific component for analyzing biological substances,
    wherein
    a portion or all of a bottom side of the micro chamber plate body is made of a transparent flowable film having the property of freely changing its shape due to its flexibility when heat, a vacuum, or pressure is applied thereto, said transparent flowable film being at a bottom side of the micro chamber holes,
    the micro chamber plate body covering part has formed therein at least one sample inlet per micro chamber hole, and
    the micro chamber plate body covering part is attached to the flowable film on the top side of the micro chamber plate body.

2. The micro chamber plate of claim 1, wherein the flowable film extends from the top side of the micro chamber plate body via a lateral side of the micro chamber holes to the bottom side of the micro chamber holes.

3. The micro chamber plate of claim 1, wherein the flowable film is at least one of heat-bonded and pressure-bonded to the micro chamber plate body.

4. A method of processing a sample for analysis, utilizing the micro chamber plate of claim 1, wherein a sample inlet is constructed and arranged to enable a sample to be supplied to the micro chamber holes in response to an applied vacuum and/or pressure, said method comprising applying vacuum and/or pressure to cause the sample to be supplied to the micro chamber holes, and the transparent flowable film to sag in response to the applied vacuum and/or pressure, and after the micro chamber holes have been supplied with sample by the applied vacuum and/or pressure, releasing said applied vacuum and/or pressure, to cause the transparent flowable film to de-sag so that extra sample or bubbles in the micro chamber holes are discharged to the outside of the micro chamber holes through the sample inlet upon said releasing.

5. The micro chamber plate of claim 1, further comprising an adhesive film having an adhesive property provided between the flowable film and the micro chamber plate body or between the flowable film and the micro chamber plate body covering part.

6. The micro chamber plate of claim 1, wherein the flowable film is made of a material selected from the group consisting of polyethylene, polyethylene terephthalate, stretched or non-stretched polypropylene, polycarbonate, PMMA, and a copolymer thereof.

7. The micro chamber plate of claim 1, wherein the micro chamber plate body covering part is made of a metal or a polymer film.

8. The micro chamber plate of claim 1, wherein the micro chamber plate body covering part is made of a porous membrane having a pore size of 0.2-5.0 μm.

9. The micro chamber plate of claim 1, wherein each sample inlet has an area of 0.05-60% based on total area of each micro chamber hole.

10. The micro chamber plate of claim 2, wherein the micro chamber plate body covering part is thermally bonded, laser bonded, or adhesive bonded to the flowable film.

11. The micro chamber plate of claim 1, wherein a surface of the micro chamber plate body is coated with at least one material selected from a polyester-based polymer resin and a polyethylene-based hot-melt adhesive.

12. The method of claim 4, wherein only vacuum is applied.

13. The method of claim 4, wherein only pressure is applied.

* * * * *

UNITED STATES PATENT AND TRADEMARK OFFICE
CERTIFICATE OF CORRECTION

PATENT NO. : 11,045,808 B2
APPLICATION NO. : 15/037672
DATED : June 29, 2021
INVENTOR(S) : Gu-Young Song et al.

It is certified that error appears in the above-identified patent and that said Letters Patent is hereby corrected as shown below:

In the Specification

Column 3, Line 33, "39.5 µl" should be -- 39.5 pl --.

Column 3, Line 54, "through-holes formed" should be -- through-holes is formed --.

Signed and Sealed this
Twenty-fourth Day of August, 2021

Drew Hirshfeld
*Performing the Functions and Duties of the
Under Secretary of Commerce for Intellectual Property and
Director of the United States Patent and Trademark Office*